United States Patent

Ebel et al.

Patent Number: 5,468,871
Date of Patent: Nov. 21, 1995

[54] PREPARATION OF N-SUBSTITUTED PYRAZOLES

[75] Inventors: Klaus Ebel; Juergen Schroeder, both of Ludwigshafen; Carsten Groening, Mannheim; Toni Dockner, Meckenheim; Hans R. Merkle, Ludwigshafen, all of Germany

[73] Assignee: BASF Aktiengesellschaft, Ludwigshafen, Germany

[21] Appl. No.: 334,613

[22] Filed: Nov. 7, 1994

Related U.S. Application Data

[63] Continuation of Ser. No. 251,040, May 31, 1994, abandoned.

[30] Foreign Application Priority Data

Jun. 8, 1993 [DE] Germany .......... 43 18 960.1
Feb. 8, 1994 [DE] Germany .......... 44 03 815.1

[51] Int. Cl.$^6$ ............................................. C07D 231/12
[52] U.S. Cl. ............................................. 548/373.1
[58] Field of Search ............................. 548/373.1

[56] References Cited

FOREIGN PATENT DOCUMENTS 0454307 10/1991 European Pat. Off. .
516982 12/1992 European Pat. Off. .
1603793 12/1971 France .

OTHER PUBLICATIONS

Tanaka et al, Chemical Letters No. 4 (1992), pp. 575–578.
Motoyama et al, Chem. Abstracts, vol. 90, No. 3 (1979), 90:22552s.
Tanaka et al, Chemistry Letters, (1992) pp. 575–578.

Primary Examiner—Robert W. Ramsuer
Attorney, Agent, or Firm—John H. Shurtleff

[57] ABSTRACT

N-substituted-pyrazoles of the formula

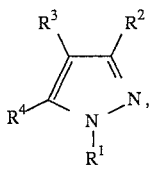

I wherein $R^1$ is $C_1$–$C_{12}$-alkyl or $C_7$–$C_{20}$-alkyl, and $R^2$, $R^3$ and $R^4$ independently denote hydrogen, $C_1$–$C_{12}$-alkyl, phenyl, $C_7$–$C_{20}$-alkylphenyl and $C_7$–$C_{20}$-phenylalkyl, are prepared by reacting a pyrazole of the formula

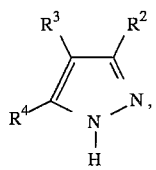

II wherein $R^2$, $R^3$ and $R^4$ have the meanings above, with an alcohol or ether of the formula

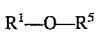

III, wherein $R^5$ is hydrogen or $R^1$, at a temperature of from 200° to 550° C. and a pressure of from 0.001 to 50 bar in the presence of a heterogeneous catalyst, preferably one which contains acid centers such as the oxides of aluminum, silicon, titanium and/or zirconium, optionally doped with phosphoric acid.

9 Claims, No Drawings

PREPARATION OF N-SUBSTITUTED PYRAZOLES

This application is a continuation of application Ser. No. 08/251,040, filed May 31, 1994 (abandoned).

The present invention relates to a process for the preparation of N-substituted pyrazoles by the reaction of pyrazoles with alcohols or ethers in the presence of a heterogeneous catalyst at elevated temperatures.

EP-A 454,307 describes a process for the N-alkylation of pyrazoles, in which N-unsubstituted pyrazoles are converted to the corresponding salts with strong bases such as sodium methylate or alkali metals, such as sodium, and are subsequently alkylated with an alkyl halide or dialkyl sulfate. Drawbacks of this process are the expensive starting materials and the large volume of salts formed.

*Chemistry Letters*, 575–578 (1992) discloses a process for the N-alkylation of pyrazoles, in which N-unsubstituted pyrazoles are caused to react with alcohols in the presence of catalytic amounts of ruthenium-, rhodium-, or iridium-/trialkyl phosphite complexes.

A drawback of this process is the high price of the catalysts.

It was the object of the present invention to overcome the aforementioned drawbacks.

Accordingly, there has been found a new and improved process for the preparation of N-substituted pyrazoles of the general formula I

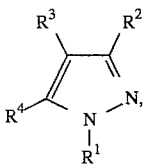
(I)

in which

R$^1$ denotes C$_1$–C$_{12}$ alkyl or C$_7$–C$_{20}$ phenylalkyl and

R$^2$, R$^3$, R$^4$ independently denote hydrogen, C$_1$–C$_{12}$ alkyl, phenyl, C$_7$–C$_{20}$ alkylphenyl, or C$_7$–C$_{20}$ phenylalkyl by the reaction of pyrazoles of the general formula II

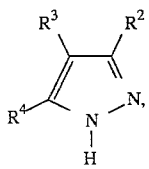
(II)

in which

R$^2$, R$^3$ and R$^4$ have the aforementioned meanings, with compounds of the general formula III

R$^1$—O—R$^5$ (III), in which

R$^1$ has the aforementioned meanings and

R$^5$ denotes hydrogen or R$^1$, in the presence of a catalyst at temperatures ranging from 200° to 550° C. and pressures of from 0.001 to 50 bar wherein the catalyst used is a heterogeneous catalyst.

The process of the invention may be carried out as follows.

The reaction can be carried out by causing contact of a pyrazole II and a compound III in the presence of a heterogeneous catalyst at temperatures ranging from 200° to 550° C., preferably from 250° to 450° C. and more preferably from 280° to 400° C. and under a pressure of from 0.001 to 50 bar, preferably from 0.01 to 5 bar and more preferably from 0.1 to 1.5 bar, usually at standard pressure (atmospheric pressure) and optionally under an inert gas such as nitrogen or argon. The temperature and pressure conditions should be such that the reaction takes place in the preferred gas phase.

Suitable catalysts are heterogeneous catalysts, particularly those having acid centers such as aluminum oxide, silicon dioxide, titanium dioxide and/or zirconium dioxide, optionally doped with from 1 to 30 wt %, in particular from 5 to 15 wt %, of phosphoric acid. γ-Aluminium oxide and silicon dioxide are preferred. The phosphoric acid can be wholly or partly present in the form of phosphorus pentoxide, orthophosphoric acid, pyrophosphoric acid, or polyphosphoric acid, eg from 72 to 88 wt % of phosphorus pentoxide, and is calculated in this case as phosphoric acid, irrespective of the actual constitution of the phosphoric acid or phosphoric anhydride.

The molar ratio of the compound III to the pyrazole II is usually from 0.01:1 to 1.1:1, preferably from 0.1:1 to 1:1 and more preferably from 0.8:1 to 0.95:1.

The reaction can be carried out by passing the starting materials II and III, heated to the temperature of reaction, over the catalyst, heated to the temperature of reaction, in a fixed bed reactor. The mixture leaving the reaction chamber can be condensed and fractionally distilled.

Compared with the prior processes the process of the invention yields N-substituted pyrazoles in a simpler and more economical manner.

The substituents R$^1$, R$^2$, R$^3$, R$^4$ and R$^5$ in the compounds I, II, and III have the following meanings, R$^1$ and R$^5$, as limited to alkyl and phenylalkyl, and R$^2$, R$^3$ and R$^4$ without such limitation independently denote C$_1$–C$_{12}$ alkyl, preferably C$_1$–C$_8$ alkyl such as methyl, ethyl, n-propyl, isopropyl, n-butyl, butyl, isobutyl, sec-butyl, tert-butyl, n-pentyl, isopentyl, sec-pentyl, neopentyl, 1,2- dimethylpropyl, n-hexyl, isohexyl, sec-hexyl, n-heptyl, isoheptyl, n-octyl, isooctyl and more preferably C$_1$–C$_4$ alkyl such as methyl, ethyl, n,-propyl, isopropyl, n-butyl, isobutyl, sec-butyl, and tert-butyl, phenyl, C$_7$–C$_{20}$ alkylphenyl, preferably C$_7$–C$_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, C$_7$–C$_{20}$ phenylalkyl, preferably C$_7$–C$_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl, and 4-phenylbutyl, more preferably benzyl, 1-phenethyl, and 2-phenethyl,

R$^2$, R$^3$, R$^4$, R$^5$ further independently denote hydrogen.

Particularly suitable starting compounds II are pyrazoles such as pyrazole, 3-methylpyrazole, 4-methylpyrazole, 3,4-dimethylpyrazole, 3,5-dimethylpyrazole, 3-ethylpyrazole, 4-ethylpyrazole, 3-phenylpyrazole, 4-phenylpyrazole, 3,4-diphenylpyrazole, 3,5-diphenylpyrazole, and 3-methyl-4-phenylpyrazole.

Particularly suitable starting compounds III are alcohols such as methanol, ethanol, n-propanol, isopropanol, and n-butanol as well as ethers such as dimethyl ether, diethyl ether, di-n-propyl ether, and diisopropyl ether.

The N-substituted pyrazoles I which can be prepared by the process of the invention are valuable starting materials for the synthesis of dyes, pharmaceuticals, and plant protectants.

EXAMPLES

Example 1

65.6 g of a mixture of 7.5 wt % of 3,5-diphenylpyrazole, 10.9 wt % of methanol, and 81.6 wt % of toluene are evaporated, per hour, and passed, together with 10 L/h (STP) of nitrogen, upwardly through a fixed bed reactor heated at 380° C. The fixed bed reactor is packed with 50 mL of a catalyst consisting of 80 wt % of γ-aluminum oxide and 20wt % silicon dioxide. The reaction gases are subsequently condensed. There are obtained, per hour, 55.7 g of organic phase containing 9.0 wt % of 1-methyl-3,5-diphenylpyrazole (96 % of theory based on 3,5-diphenylpyrazole used).

Example 2

65.6 g of a mixture of 7.5 wt % of 3,5-diphenylpyrazole, 10.9 wt % of methanol, and 81.6 wt % of toluene are evaporated, per hour, and passed, together with 10 L/h (STP) of nitrogen, upwardly through a fixed bed reactor heated at 410° C. The fixed bed reactor is packed with 50 mL of a catalyst consisting of 80 wt % of γ-aluminum oxide and 20 wt % silicon dioxide. The reaction gases are subsequently condensed. There are obtained, per hour, 57.3 g of organic phase containing 8.6 wt % of 1-methyl-3,5-diphenylpyrazole (94% of theory based on 3,5-diphenylpyrazole used).

Example 3

87.0 g of a mixture of 6.0 wt % of 3,5-diphenylpyrazole, 12.5 wt % of ethanol, and 81.5 wt % of toluene are evaporated, per hour, and passed, together with 10 L/h (STP) of nitrogen, upwardly through a fixed bed reactor heated at 410° C. The fixed bed reactor is packed with 50 mL of a catalyst consisting of 80 wt % of γ-aluminum oxide and 20 wt % silicon dioxide. The reaction gases are subsequently condensed. There are obtained, per hour, 74.4 g of organic phase containing 1.4 wt % of 1-methyl-3,5-diphenylpyrazole and 5.9 wt % of 1-ethyl-3,5-diphenylpyrazole (94% of theory based on 3,5-diphenylpyrazole used).

Example 4

87.0 g of a mixture of 6.0 wt % of 3,5-diphenylpyrazole, 12.5 wt % of methanol, and 81.5 wt % of toluene are evaporated, per hour, and passed, together with 10 L/h (STP) of nitrogen, upwardly through a fixed bed reactor heated at 450° C. The fixed bed reactor is packed with 50 mL of a catalyst consisting of 80 wt % of γ-aluminum oxide and 20 wt % silicon dioxide. The reaction gases are subsequently condensed. There are obtained, per hour, 72.9 g of organic phase containing 2.3 wt % of 1-methyl-3,5-diphenylpyrazole and 5.0 wt % of 1-ethyl-3,5-diphenylpyrazole (92% of theory based on 3,5-diphenylpyrazole used).

Example 5

25.5 g of a mixture of 12.2 wt % of 3-phenylpyrazole, 27.2 wt % of methanol, and 60.6 wt % of toluene are evaporated, per hour, and passed, together with 10 L/h (STP) of nitrogen, upwardly through a fixed bed reactor heated at 410° C. The fixed bed reactor is packed with 50 mL of a catalyst consisting of 80 wt % of γ-aluminum oxide and 20 wt % silicon dioxide. The reaction gases are subsequently condensed. There are obtained, per hour, 19.0 g of organic phase containing 16.9 wt % of 1-methyl-3-phenylpyrazole/1-methyl-5-phenylpyrazole (95% of theory based on 3-phenylpyrazole used).

Example 6

22.5 g of a mixture of 58.5 wt % of methanol and 41.5 wt % of pyrazole are evaporated, per hour, and passed, together with 10 L/h (STP) of nitrogen, upwardly through a fixed bed reactor heated at 300° C. The fixed bed reactor is packed with 100 mL of a catalyst consisting of 95 wt % of γ-aluminum oxide and 5 wt % of phosphoric acid. The reaction gases are subsequently condensed. There are obtained, per hour, 17.0 g of condensate containing 65.2 wt % of 1-methylpyrazole (99% of theory based on pyrazole used).

Example 7

22.5 g of a mixture of 58.5 wt % of methanol and 41.6 wt % of pyrazole are evaporated, per hour, and passed, together with 10 L/h (STP) of nitrogen, upwardly through a fixed bed reactor heated at 450° C. The fixed bed reactor is packed with 100 mL of a catalyst consisting of 95 wt % of γ-aluminum oxide and 5 wt % of phosphoric acid. The reaction gases are subsequently condensed. There are obtained, per hour, 18.4 g of condensate containing 41.8 wt % of 1-methylpyrazole and 11.7 wt % of 1.4-dimethylpyrazole (16% of theory based on pyrazole used).

Example 8

21.5 g of a mixture of 66.1 wt % of methanol and 33.9 wt % of 4-methylpyrazole are evaporated, per hour, and passed, together with 10 L/h (STP) of nitrogen, upwardly through a fixed bed reactor heated at 400° C. The fixed bed reactor is packed with 100 mL of a catalyst consisting of 90 wt % of silicon dioxide and 10 wt % of γ-aluminum oxide. The reaction gases are subsequently condensed. There are obtained, per hour, 15.5 g of condensate containing 52.3 wt % of 1,4-dimethylpyrazole (95% of theory based on 4-methylpyrazole used).

Example 9

111.3 g of a mixture of 53.9 wt % of methanol and 46.1 wt % of 4-methylpyrazole are evaporated, per hour, and passed, together with 10 L/h (STP) of nitrogen, upwardly through a fixed bed reactor heated at 400° C. The fixed bed reactor is packed with 100 mL of a catalyst consisting of 90 wt % of γ-aluminum oxide and 10 wt % of silicon dioxide. The reaction gases are subsequently condensed. There are obtained, per hour, 91.7 g of condensate containing 3.2 wt % of 4-methylpyrazole and 57.0 wt % of 1,4-dimethylpyrazole (87% of theory based on 4-methylpyrazole used).

Example 10

43.8 g of a mixture of 67.0 wt % of ethanol and 33.0 wt % of pyrazole are evaporated, per hour, and passed, together with 10 L/h (STP) of nitrogen, upwardly through a fixed bed reactor heated at 400° C. The fixed bed reactor is packed with 100 mL of a catalyst consisting of 90 wt % of γ-aluminum oxide and 10 wt % of silicon dioxide. The reaction gases are subsequently condensed. There are obtained, per hour, 31.7 g of condensate containing 0.2 wt % of pyrazole and 62.2 wt % of 1-ethylpyrazole (97% of theory based on pyrazole used).

Example 11

66.4 g of a mixture of 53.9 wt % of methanol and 46.1 wt % of 3-methylpyrazole are evaporated, per hour, and passed, together with 10 L/h (STP) of nitrogen, upwardly through a fixed bed reactor heated at 400° C. The fixed bed reactor is packed with 100 mL of a catalyst consisting of 90 wt % of γ-aluminum oxide and 10 wt % of silicon dioxide. The reaction gases are subsequently condensed. There are obtained, per hour, 53.4 g of condensate containing 1.0 wt % of 3-methylpyrazole and 56.7 wt % of 1,3-dimethylpyrazole/1,5-dimethylpyrazole (84% of theory based on 3-methylpyrazole used).

Example 12

21.3 g of a mixture of 68.7 wt % of isopropanol and 31.3 wt % of 3-methylpyrazole are evaporated, per hour, and passed, together with 10 L/h (STP) of nitrogen, upwardly through a fixed bed reactor heated at 300° C. The fixed bed reactor is packed with 100 mL of a catalyst consisting of 90 wt % of γ-aluminum oxide and 10 wt % of silicon dioxide. The reaction gases are subsequently condensed. There are obtained, per hour, 8.6 g of condensate containing 20.2 wt % of 4-methylpyrazole and 60.8 wt % of 1-isopropy-3-methyllpyrazole/1-isopropyl-5-methylpyrazole (67% of theory based on 3-methylpyrazole used).

Example 13

39.0 g of a mixture of 73.0 wt % of diethyl ether and 27.0 wt % of 3-methylpyrazole are evaporated, per hour, and passed, together with 10 L/h (STP) of nitrogen, upwardly through a fixed bed reactor heated at 400° C. The fixed bed reactor is packed with 100 mL of a catalyst consisting of 90 wt % of γ-aluminum oxide and 10 wt % of silicon dioxide. The reaction gases are subsequently condensed. There are obtained, per hour, 20.3 g of condensate containing 3.3 wt % of 3-methylpyrazole and 58.1 wt % of 1-ethyl-3-methylpyrazole/1-ethyl-5-methylpyrazole (96% of theory based on 3-methylpyrazole used).

We claim:
1. A process for the preparation of N-substituted-pyrazoles of the formula

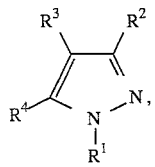

I wherein $R^1$ is $C_1$–$C_{12}$-alkyl or $C_7$–$C_{20}$-phenylalkyl and $R^2$, $R^3$ and $R^4$ independently denote hydrogen, $C_1$–$C_{12}$-alkyl, phenyl, $C_7$–$C_{20}$-alkylphenyl and $C_7$–$C_{20}$-phenylalkyl, which comprises:
reacting a pyrazole of the formula

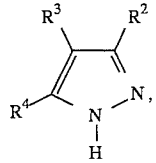

II wherein $R^2$, $R^3$ and $R^4$ have the meanings above, with an alcohol or ether of the formula

III, wherein $R^5$ is hydrogen or $R^1$, at a temperature of from 200° to 550° C. and a pressure of from 0.001 to 50 bar in the presence of a heterogeneous catalyst selected from the group consisting of aluminum oxide, dioxide, titanium dioxide, zirconium dioxide and mixtures thereof, said catalyst being optionally doped with phosphoric acid.

2. A process as claimed in claim 1, wherein the molar ratio of the pyrazole II to the compound III is from 0.01:1 to 1.1:1.

3. A process as claimed in claim 1, wherein the molar ratio of the pyrazole II to the compound III is from 0.1:1 to 1:1.

4. A process as claimed in claim 1, wherein the molar ratio of the pyrazole II to the compound III is from 0.8:1 to 0.95:1.

5. A process as claimed in claim 1, wherein the catalyst is silicon dioxide.

6. A process as claimed in claim 1, wherein the catalyst is γ-aluminum oxide.

7. A process as claimed in claim 1, wherein the catalyst is a mixture of silicon dioxide and γ-aluminum oxide.

8. A process as claimed in claim 1, wherein the pyrazole reactant II is pyrazole, 3-methylpyrazole, 4-methylpyrazole, 3,4-dimethylpyrazole, 3,5-dimethylpyrazole, 3-ethylpyrazole, 4-ethylpyrazole, 3-phenylpyrazole, 4-phenylpyrazole, 3,4-diphenylpyrazole, 3,5-diphenylpyrazole or 3-methyl-4-phenylpyrazole.

9. A process as claimed in claim 1, wherein the reactant compound III is methanol, ethanol, n-propanol, isopropanol, n-butanol, dimethyl ether, diethyl ether, di-n-propyl ether or diisopropyl ether.

* * * * *

UNITED STATES PATENT AND TRADEMARK OFFICE
CERTIFICATE OF CORRECTION

PATENT NO. : 5,468,871
DATED : November 21, 1995
INVENTOR(S) : Ebel, et. al.

It is certified that error appears in the above-indentified patent and that said Letters Patent is hereby corrected as shown below:

Column 6, Claim 1, line 23, after "aluminum oxide," and before "dioxide"; insert the word --silicon--.

Signed and Sealed this

Ninth Day of April, 1996

Attest:

BRUCE LEHMAN

*Attesting Officer*    *Commissioner of Patents and Trademarks*